United States Patent [19]

Schoffel

[11] Patent Number: 4,461,185
[45] Date of Patent: Jul. 24, 1984

[54] INJECTION NEEDLE
[75] Inventor: Rainer Schoffel, Frickingen, Fed. Rep. of Germany
[73] Assignee: Bodenseewerk Perkin-Elmer & Co., GmbH, Uberlingen, Fed. Rep. of Germany
[21] Appl. No.: 437,233
[22] Filed: Oct. 28, 1982

Related U.S. Application Data
[63] Continuation of Ser. No. 392,120, Jun. 25, 1982, abandoned.

[30] Foreign Application Priority Data

Jun. 27, 1981 [DE] Fed. Rep. of Germany ....... 3125321

[51] Int. Cl.³ ............................................. G01N 1/10
[52] U.S. Cl. .............................. 73/864.01; 73/864.74
[58] Field of Search ........... 73/864.81, 864.84, 864.85, 73/864.86, 864.87, 864.01, 864.74, 864.73, 863.85

[56] References Cited

U.S. PATENT DOCUMENTS 3,754,434  8/1975  Guild ............................... 73/864.81

Primary Examiner—S. Clement Swisher
Attorney, Agent, or Firm—F. L. Masselle; E. T. Grimes; R. A. Hays

[57] ABSTRACT

A needle, for use in withdrawing a liquid sample from sample vessels closed by self-sealing diaphragms, includes a capillary tube 12 turned inwardly at its end. The end thereof is tapered conically at the inside as well as at the outside.

2 Claims, 1 Drawing Figure

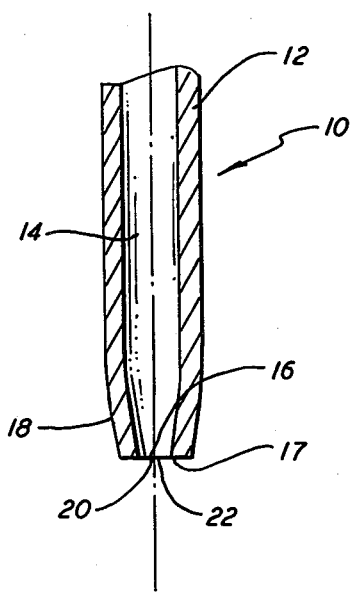

INJECTION NEEDLE

This Application is a continuation of Application Serial No. 392,120, filed June 25, 1982 now abandoned.

BACKGROUND OF THE INVENTION

The present invention generally relates to a needle for taking up a liquid sample from a closed sample vessel having a self-sealing diaphragm and, in particular, relates to a needle comprised of a capillary tube one end of which has a tapered interior.

German Patent Application No. P 30 37 014 (not pre-published) corresponding to U.S. Patent Application Ser. No. 304,735 filed Sept. 23, 1981 now U.S. Pat. No. 4,393,726 and assigned to the assignee hereof, describes a method for supplying a liquid sample by means of a needle or injection needle having a pointed end. Therein the injection needle is made by laterally bending the end of a capillary and by cutting off this bent-off end at an angle so that the injection needle has a tip substantially on its longitudinal axis and a longitudinal passage turning at the end and opening laterally. The longitudinal passage is of substantially constant cross-section up to its mouth. In taking up a sample into the longitudinal passage of the needle or injection needle, a meniscus of the sample liquid is formed above the outer surface of the needle at the mouth thereof due to the surface tension of the sample liquid. In removing the needle, this meniscus is stripped off by the self-sealing diaphragm. Thereby, the amount of sample being taken is changed in an uncontrolled way and the measurement becomes incorrect. Further, when samples are repeatedly taken from the same sample vessel, the sample remaining on the self-sealing diaphragm can, over a period of time, crystallize due to evaporation of the solvent or contaminate subsequent samples.

Needles are also known in which the capillary tube is closed by means of a conical closing member at its end, the member usually having a lateral aperture for taking up and delivering liquid (leaflet Spitzentyp 5 from the Hamilton Monaduz Company catalogue "Prazisions-Instrumente zur Messung und Dosierung von Flussigkeiten und Gasen"). In this case, however, the strip-off effect occurs as well. Also, some of the sample remains in the sample vessel and cannot be taken up by the needle through the lateral aperture thereof.

Furthermore, another needle described in the above-mentioned printed publication by Hamilton has its tip electrolytically tapered on its outside. Therein, however, the longitudinal passage is a straight passage of continuous constant cross-sectional opening in the end face. With such a needle design, there is the danger that material is punched out from the self-sealing diaphragm and either plugs the needle or crumbles into the sample.

SUMMARY OF THE INVENTION

Accordingly, it is one object of the present invention to provide a needle which avoids both the plugging thereof by material of the diaphragm as well as avoids the stripping therefrom of sample liquid.

This object is achieved, at least in part, by a capillary tube needle one end thereof having the interior conically tapered.

In one needle embodying the principles of the present invention, the inlet of the longitudinal passage is provided at the end face thereof, and its interior cross-section is reduced compared to the other portions of the longitudinal passage. Thereby, stripping off of sample liquid is avoided. The reduced cross-section of the inlet also prevents punching out material from the self-sealing diaphragm thus avoiding the danger of plugging of the needle.

Other objects and advantages of the present invention will become apparent to those skilled in the art from the following detailed description of the invention and the attached drawing.

BRIEF DESCRIPTION OF THE DRAWING

The single FIGURE of the drawing is a cross-sectional illustration of a needle, not drawn to scale, embodying the principles of the present invention.

DETAILED DESCRIPTION OF THE INVENTION

A needle, generally indicated at 10 in the drawing and embodying the principles of the present invention, includes a capillary tube 12 having a longitudinal passage 14 therein. The needle 10 further includes a portion 16 at one end 17 thereof which portion includes a conically tapered outer surface 18. Additionally, and most importantly, the longitudinal passage 14 of the portion 16 at one end 17 of the capillary tube 12 is conically tapered as well. That is, the portion 16 is conically tapered at the inside. Preferably, the inner surface 20 of the longitudinal passage 14 has substantially the same conic taper as the outer surface 18.

In one specific embodiment, the capillary tube 12 has an outer diameter of about 0.71 millimeters and an inside diameter, i.e., the longitudinal passage 14, of about 0.41 millimeters. The portion 16 has a length of about 0.5 millimeters. The portion 16 is tapered to a conus angle of about 22 degrees to form an aperture 22 at the one end 17 thereof of about 0.2 millimeters.

The desired taper may be formed by inserting the capillary tube 12 in a lathe and turning the portion 16 by means of a roller. Of course, other techniques known in the art could also be employed.

Although the present invention has been discussed herein with respect to one embodiment, it will be understood by persons skilled in the art that other configurations are also possible. Thus, this description is deemed to be exemplary only and not limiting and the invention is considered defined by the appended claims and the reasonable interpretation thereof.

What is claimed is:
1. Needle for use in withdrawing a liquid sample from a closed sample vessel having a self-sealing diaphragm, said needle comprising:
   a capillary tube having an aperture at one end thereof, which aperture communicates with a longitudinal passage through said tube, said one end being conically tapered at the outside, the interior of said capillary tube being conically tapered at said one end, said taper having a conus angle of about 22° and being such that the diameter of said aperture is about equal to half the diameter of said passage.
2. Needle as claimed in claim 1 wherein said capillary tube is turned inwardly at said one end.